(12) United States Patent
Lee et al.

(10) Patent No.: US 8,146,447 B2
(45) Date of Patent: Apr. 3, 2012

(54) CONTAMINATION ANALYSIS UNIT AND METHOD THEREOF, AND RETICLE CLEANING SYSTEM

(75) Inventors: Ok-Sun Lee, Gyeonggi-do (KR); Hyung-Seok Choi, Gyeonggi-do (KR); Yo-Han Ahn, Gyeonggi-do (KR); Ji-Young Kim, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 707 days.

(21) Appl. No.: 12/031,086

(22) Filed: Feb. 14, 2008

(65) Prior Publication Data

US 2008/0196515 A1    Aug. 21, 2008

(30) Foreign Application Priority Data

Feb. 15, 2007 (KR) .................. 10-2007-0016070

(51) Int. Cl.
*G01N 1/14* (2006.01)
(52) U.S. Cl. ................................... 73/863.83
(58) Field of Classification Search ............... 73/863.83, 73/864.81, 864.91
See application file for complete search history.

(56) References Cited

U.S. PATENT DOCUMENTS

| | | | | |
|---|---|---|---|---|
| 4,347,749 A | * | 9/1982 | Heintze | 73/863.21 |
| 5,368,054 A | * | 11/1994 | Koretsky et al. | 134/153 |
| 7,597,012 B2 | * | 10/2009 | Yao et al. | 73/863.21 |
| 2007/0035715 A1 | * | 2/2007 | Choi et al. | 355/75 |
| 2008/0028873 A1 | * | 2/2008 | Yao et al. | 73/863.23 |
| 2008/0145797 A1 | * | 6/2008 | Verbeke et al. | 430/322 |
| 2009/0059217 A1 | * | 3/2009 | Okita | 356/237.5 |

FOREIGN PATENT DOCUMENTS

| | | |
|---|---|---|
| JP | 09-106065 | 4/1997 |
| JP | 2003-068817 | 3/2003 |
| JP | 2005-202135 | 7/2005 |
| KR | 1020000067357 A | 11/2000 |
| KR | 1020060032908 A | 4/2006 |
| KR | 100612329 B1 | 8/2006 |

OTHER PUBLICATIONS

Notice to File a Response/Amendment to the Examination Report corresponding to Korean Application No. 10-2007-0016070 mailed Jan. 18, 2008.
Notice of Allowance corresponding to Korean Application No. 10-2007-0016070 mailed May 14, 2008.

* cited by examiner

*Primary Examiner* — Hezron E Williams
*Assistant Examiner* — Tamiko D Bellamy
(74) *Attorney, Agent, or Firm* — Myers Bigel Sibley & Sajovec, PA

(57) ABSTRACT

A contamination analysis unit and method for inspecting pollutants remaining on a target side of an inspection object such as a reticle after cleaning the object is provided. After steeping the target side in a solution, a sampling liquid may be abstracted therefrom after a predetermined time and may be analyzed.

15 Claims, 15 Drawing Sheets

CONTAMINATION ANALYSIS UNIT AND METHOD THEREOF, AND RETICLE CLEANING SYSTEM

CROSS-REFERENCE TO RELATED APPLICATIONS

This U.S. non-provisional patent application claims priority under 35 U.S.C. §119 of Korean Patent Application No. 10-2007-0016070 filed on Feb. 15, 2007, the disclosure of which is incorporated herein by reference in its entirety.

FIELD AND BACKGROUND OF THE INVENTION

The present invention relates to systems and methods for manufacturing substrates. More particularly, the present invention relates to a contamination analysis unit and method for inspecting pollutants remaining on the surface of a cleaned reticle, and a reticle cleaning system.

Semiconductor devices are fabricated by way of plural processes such as ion implantation, deposition, diffusion, photolithography, etching, and so forth. Among those processing steps, photolithography is used for shaping designed patterns on a wafer. Photolithography is carried out by conducting the steps of coating a photoresist film on a wafer, exposing the wafer by transcribing the mask pattern into the photoresist film on the wafer, and then developing the pattern on the wafer by removing the photoresist film from specific regions thereon.

In the exposing step, a reticle is used as a mask that has a circuit pattern. During the exposing step, a pellicle (i.e., a thin and transparent film) is adhered to the reticle in order to protect the surface of the reticle from pollutants such as floating particles. The reticle is cleaned of pollutants at various periods of time. Often a first pellicle is removed from the reticle to clean the reticle and a new pellicle is then adhered to the reticle after cleaning the reticle.

With an increase of integration density in semiconductor devices, the reliability and yield thereof becomes lower due to pollutants on the molecular level that have not previously been considered as troublesome contamination. This is a particular concern when conducting the exposing step under the condition that various pollutants, e.g., ammoniums ($NH_3$), sulfuric acids ($SO_x$), or organic substances, remain on the reticle. Light irradiation of the reticle can induce optical reactions of the pollutants, and a haze on the surface of the reticle results. This degrades transmissivity of the reticle, and may result in detrimental critical dimension or pattern bridging effects on a pattern formed by the photoresist film.

To prevent these problems related to the reticle, one usually analyzes contamination on the surface of the reticle, on which light is irradiated, (hereinafter, referred to as the 'target side') after cleaning the reticle. Generally, a unit for cleaning the reticle and a unit for analyzing contamination of the reticle are provided at respective independent stations. After cleaning the reticle by a reticle cleaning system, an operator requests contamination analysis of the reticle from the contamination analysis station and then is informed of an analyzed result. Thus, it can take significant time for the operator to be informed of the analyzed result after cleaning the reticle, so that a number of reticles must be prepared in order to enhance the rate of operation of an exposing unit.

In the meantime, the contamination analysis to the reticle surface is generally carried out such that the target side of the reticle is placed face upward and a small amount of deionized water at room temperature is supplied to the target side. After a predetermined time when the deionized water is supplied, the deionized water on the target side of the reticle is delivered to an analysis unit such as a high-performance ion chromatography (HPIC) analyzer for examining contamination.

SUMMARY OF THE INVENTION

The present invention is directed to a contamination analysis unit and method capable of improving inspection reliability in analyzing pollutants remaining on a target side of a reticle after cleaning the reticle.

The present invention is also directed to a contamination analysis unit and method capable of shortening the time for analyzing pollutants remaining on a target side of a reticle after cleaning the reticle.

The present invention is further directed to a reticle cleaning system and method capable of improving reliability in cleaning a reticle and improving process efficiency in semiconductor fabrication exposing processes.

According to an embodiment of the invention, there may be provided a contamination analysis unit for inspecting pollutants on a target side of an inspection object. The unit may comprise a sampling module abstracting a sampling liquid by contacting the target side of the inspection object with a solution and an analyzer configured to analyze pollutants from the sampling liquid. The sampling module may include a liquid tub having a containing space that accommodates the target side of the inspection object while in the solution and a liquid supply nozzle configured to supply the solution into the containing space of the liquid tub.

The sampling module may further comprise a chamber providing a space that is isolated from the external environment. The chamber may include a housing with a side having a path through which the inspection object is introduced and a door opening and closing the path.

The sampling module may further include a purge gas supplying member configured to supply a purge gas into the chamber.

The sampling module may further include a heating member configured to heat the solution accommodated in the containing space. The sampling module may further include a temperature detecting member sensing temperature of the solution accommodated in the containing space.

According to one embodiment, the containing space may have a groove formed at the upper side of the liquid tub, and the door may be placed on the top of the housing, opposite to the containing space.

The liquid tub may include stay projections supporting the inspection object in the containing space so as to isolate the target side of the inspection object from the bottom of the containing space.

The sampling module may further include a liquid supply pipe providing the solution to the liquid supply nozzle and a valve installed in the liquid supply pipe which may open and close an internal path.

In addition, the sampling module may further include an exhaust pipe connecting the containing space to the analyzer so as to deliver the abstracted sampling liquid to the analyzer.

According to another embodiment, the sampling module may be shaped to abstract or collect the sampling liquid from a reticle that is used in a semiconductor process as the inspection object.

The present invention also provides a method for analyzing contamination in a target side of an inspection object that may be carried out by obtaining a sampling liquid by steeping or soaking for a period of time the target side of the inspection object in the liquid tub solution, and analyzing contamination through inspecting the sampling liquid.

According to an embodiment, the method may comprise filling the solution in a containing space formed on the top of the liquid tub and steeping the target side of the inspection object in the solution after facing the target side of the inspection object toward the liquid tub solution, so that the side opposite that of the target side is apart from and not in contact with the solution.

The target side of the inspection object may contact with the solution in a space airtight to the external environment, and a purge gas may spread in the space while the inspection object is accessing the space.

According to another embodiment, the target side of the inspection object may be steeped into a heated solution. The solution may be heated while the target side of the inspection object is steeping in the solution.

In addition, an opening time of a valve installed in a liquid supply pipe for supplying the solution into the containing space may be regulated by a controller so as to provide an uniform amount of the solution filling the containing space.

Another embodiment of the present invention may be a reticle cleaning system. The system may be comprised of a cleaning apparatus configured to clean a reticle and a contamination analysis unit configured to inspect pollutants remaining on a target side of the reticle that has been washed by the cleaning apparatus. The contamination analysis unit may include a chamber; a liquid tub provided in the chamber, including a containing space accommodating the target side of the reticle; a liquid supply nozzle configured to supply a solution into the containing space of the liquid tub; and an analyzer configured to analyze pollutants from a sampling liquid obtained by steeping the target side of the reticle in the solution.

The chamber may include a housing including the liquid tub, a path for the reticle; and a door for opening and closing the path. The contamination analysis unit may further include a purge gas supplying member configured to supply a purge gas into the chamber.

The contamination analysis unit may further include a heating member configured to heat the solution in the containing space.

According to another embodiment, the contamination analysis unit may further include a liquid supply pipe configured to supply the solution to the liquid supply nozzle and a valve installed in the liquid supply pipe; the valve opening and closing an internal path. The system may further include a controller operating to control an opening time of the valve.

According to another embodiment, the system may further include a controller for receiving an analyzed result from the analyzer and for adjusting a recipe of the cleaning apparatus with reference to the analyzed result. The reticle cleaning system may further include an alarm configured to alarm in response to the analyzed result provided from the analyzer.

Still another aspect of the present invention is a reticle cleaning method. This method may be comprised of: cleaning reticles by means of a cleaning apparatus; inspecting pollutants remaining on a target side of a selected reticle; and adjusting a recipe of the cleaning apparatus with reference to a result of the inspection. Inspecting the pollutants may be carried out by steeping the target side of the reticle in a liquid tub, abstracting a sampling liquid from the reticle, and analyzing contamination of the sampling liquid.

The solution may be heated while the target side of the reticle is steeping in the solution.

The reticle may be re-cleaned by the cleaning apparatus if the inspection result is out of a predetermined permissible range. An alarm may be generated if the inspection result is out of the permissible range.

A further understanding of the nature and advantages of the present invention herein may be realized by reference to the remaining portions of the specification and the attached drawings.

BRIEF DESCRIPTION OF THE FIGURES

The above and other features and advantages of the present invention will become more apparent by describing in detail exemplary embodiments thereof with reference to the attached drawings in which.

DETAILED DESCRIPTION OF THE EMBODIMENTS

Figure 1:
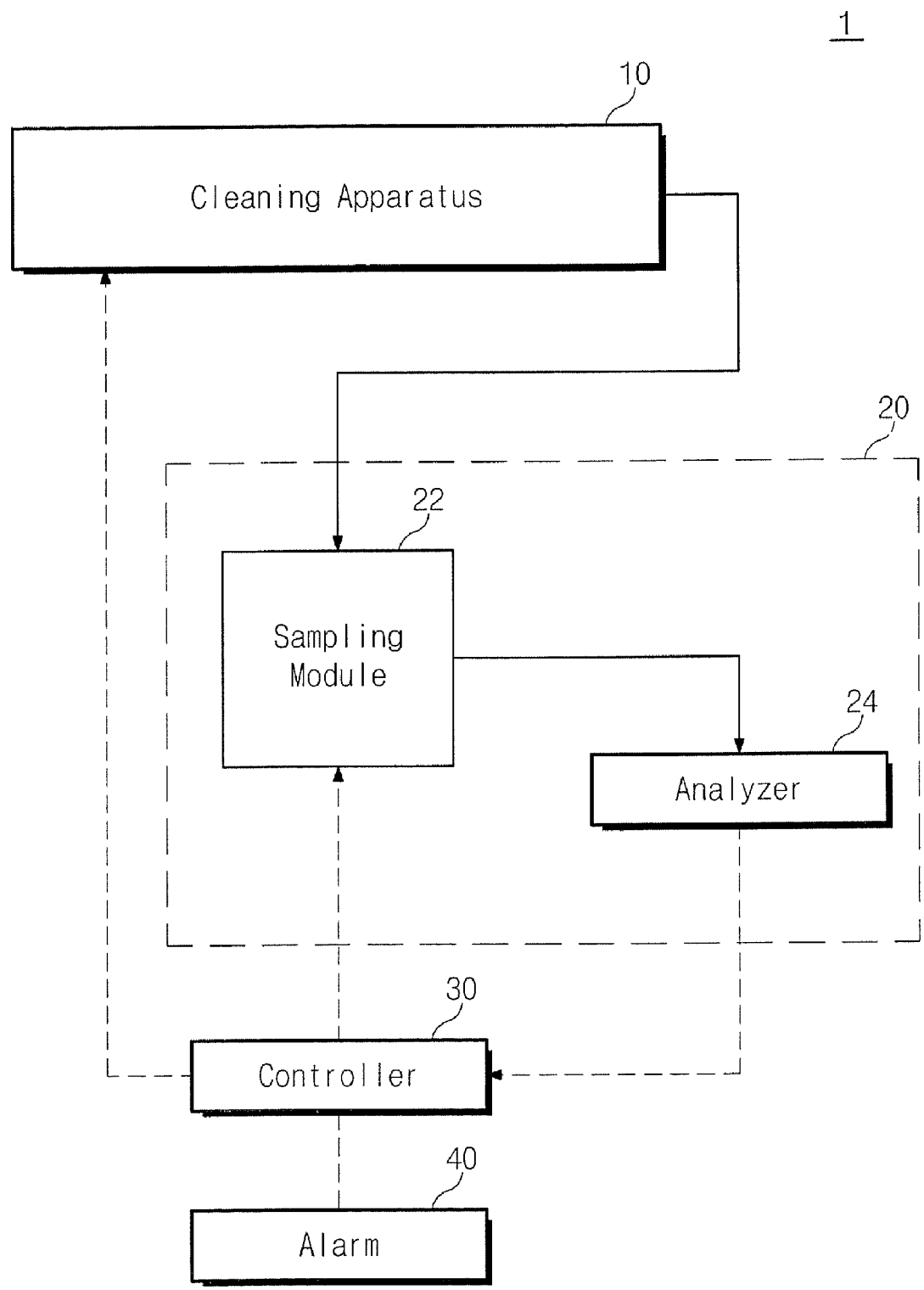
FIG. 1 is a schematic diagram showing an organization of a reticle cleaning system in accordance with an embodiment of the present invention.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout the description of the figures.

It will be understood that when an element is referred to as being "on" another element, it can be directly on the other element or intervening elements may be present. In contrast, when an element is referred to as being "directly on" another element, there are no intervening elements present. It will be understood that when an element is referred to as being "connected" or "coupled" to another element, it can be directly connected or coupled to the other element or intervening elements may be present. In contrast, when an element is referred to as being "directly connected or coupled" to another element, there are no intervening elements present. Furthermore, "connected" or "coupled" as used herein may include wirelessly connected or coupled. As used herein, the term "and/or" includes any and all combinations of one or more of the associated listed items.

It will be understood that, although the terms first, second, etc. may be used herein to describe various elements, these elements should not be limited by these terms. These terms are only used to distinguish one element from another. For example, a first layer could be termed a second layer, and, similarly, a second layer could be termed a first layer without departing from the teachings of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to other elements as illustrated in the Figures. It will be understood that relative terms are intended to encompass different orientations of the device in addition to the orientation depicted in the Figures. For example, if the device in one of the figures were turned over, elements described as being on the "lower" side of other elements would then be oriented on "upper" sides of the other elements. The exemplary term "lower", can therefore, encompass both an orientation of "lower" and "upper," depending of the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

In the description, a term "substrate" used herein may include a structure based on a semiconductor, having a semiconductor surface exposed. It should be understood that such a structure may contain silicon, silicon on insulator, silicon on sapphire, doped or undoped silicon, epitaxial layer supported by a semiconductor substrate, or another structure of a semiconductor. And, the semiconductor may be silicon-germanium, germanium, or germanium arsenide, not limited to silicon. In addition, the substrate described hereinafter may be one in which regions, conductive layers, insulation layers, their patterns, and/or junctions are formed.

Figure 3:
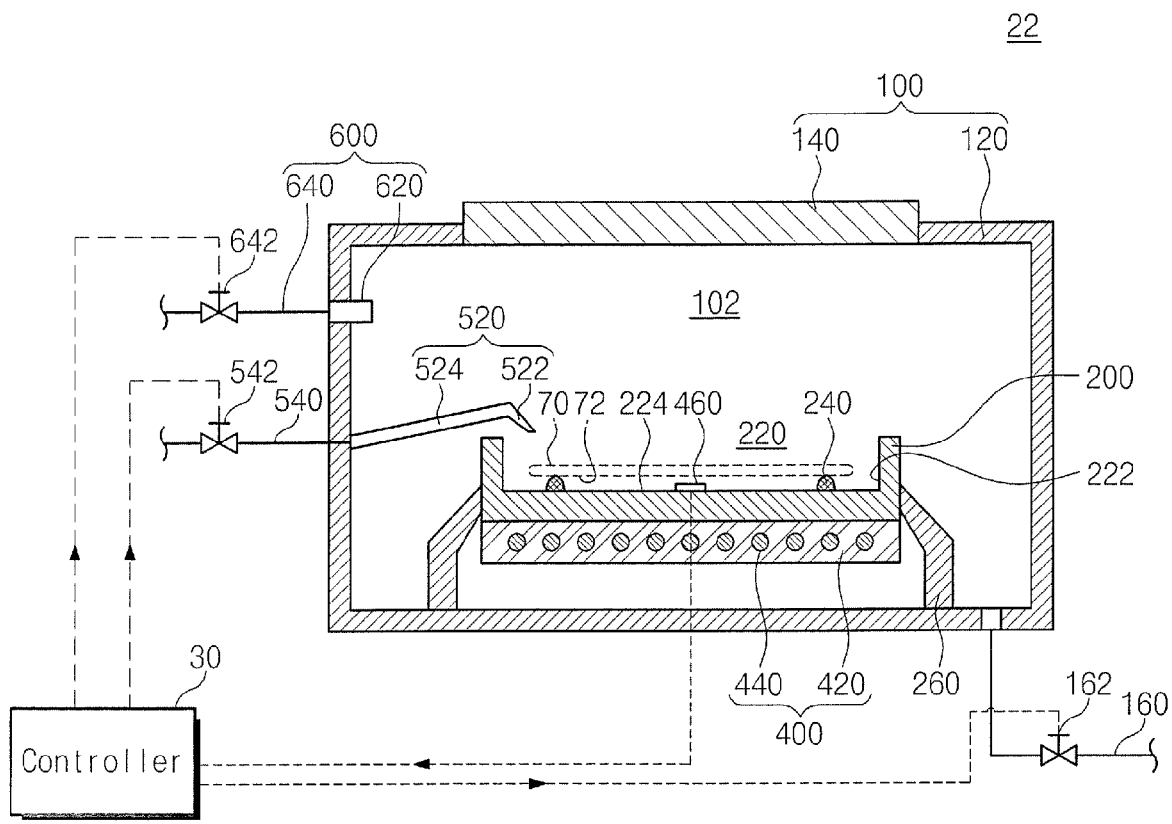
FIG. 3 is a sectional diagram schematically illustrating an embodiment of the sampling module shown in FIG. 1.

FIG. 1 is a schematic diagram showing a reticle cleaning system 1 in accordance with an embodiment of the present invention. Referring to FIG. 1, the reticle cleaning system 1 may be comprised of a cleaning apparatus 10, a contamination analysis unit 20, and a controller 30. The cleaning apparatus 10 may be operated to clean the reticle 70 (FIG. 3) wherein a pellicle (not shown) is removed from the surface on which light is irradiated, after the substrate is subjected to an exposing process. After the exposing process, the pellicle is removed from the surface on which light is irradiated. This irradiated surface of the reticle is referred to as a 'target side' 72 (FIG. 3). The contamination analysis unit 20 inspects pollutants on the target side 72 of the cleaned reticle 70. The controller 30 may receive an inspection result from the contamination analysis unit 20 and then may adjust a cleaning recipe of the cleaning apparatus 10 in accordance with the inspection result.

Figure 2:
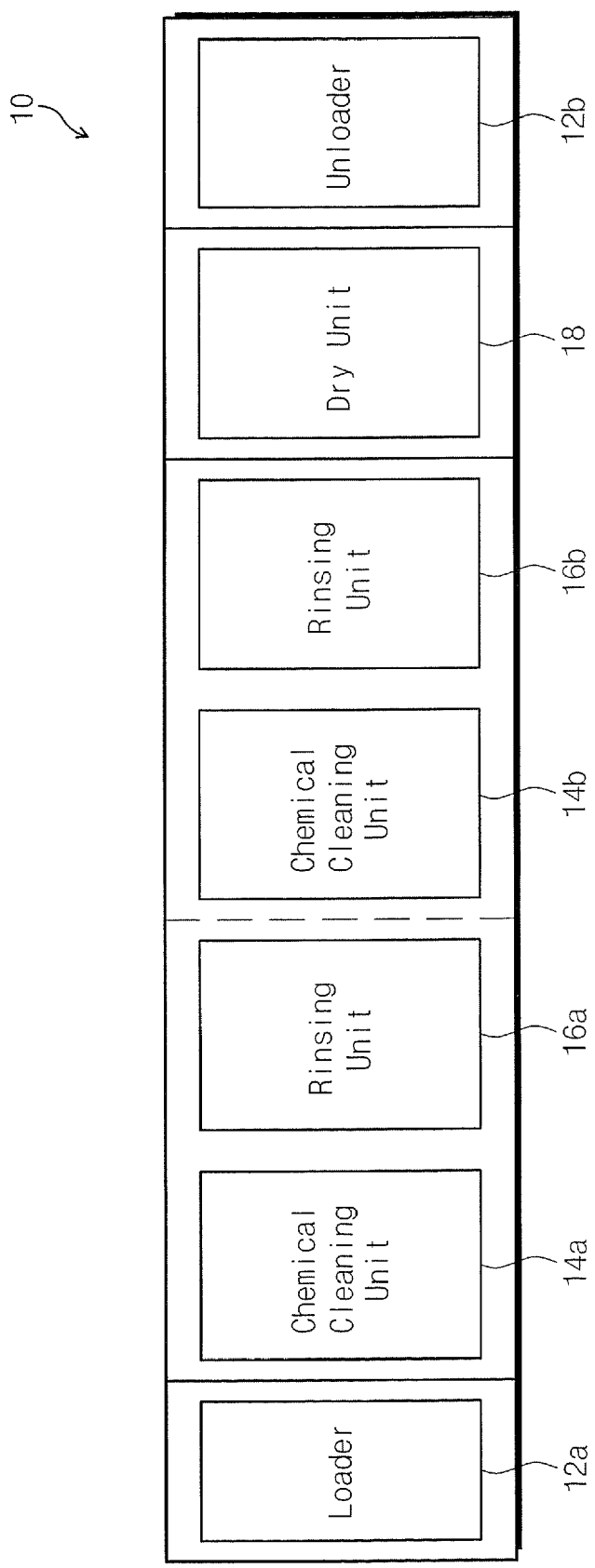
FIG. 2 is a schematic diagram showing an organization of the cleaning apparatus shown in FIG. 1.

Hereinafter will be described the structures of the members shown in FIG. 1. FIG. 2 schematically shows an organization of the cleaning apparatus 10 shown in FIG. 1. Referring to FIG. 2, the cleaning apparatus 10 may include a loader 12a, a cleaning section 13, and an unloader 12b. A reticle (not shown) used in a semiconductor fabrication exposing process may be introduced into the cleaning apparatus 10 by way of the loader 12a. After removing pollutants from the surface (i.e., the target side) of the reticle, the pollutants flow out of the cleaning apparatus 10 through the unloader 12b. The cleaning apparatus 10 may be organized as plural cleaning units 14a, 14b, 16a, 16b, and 18. The cleaning apparatus 10 may include the chemical cleaning units 14a and 14b for chemically cleaning the reticle 70, the rinsing units 16a and 16b for rinsing the reticle by deionized water at room temperature or higher, and the dry unit 18 for drying the reticle. The liquid or solution for cleaning the reticle may be made of ammonia liquor, sulfuric acid, fluoric acid, nitric acid, SC-1 (ammonia-hydrogen peroxide mixture), or SC-2 (hydrochloric acid-hydrogen peroxide mixture). Drying may be carried out by means of isopropyl-alcohol vapor. Each of the units 14a to 18 may be configured for the steeping of the reticle in a solution or rinsing liquid, or for supplying a solution or rinsing liquid to the reticle that is rotating. The units 14a to 18 may be configured to repeat the liquid cleaning and the rinsing in sequence a plurality of times, and the cleaned reticle may be dried.

The contamination analysis unit 20 may be configured to inspect pollutants remaining on the target side of the reticle that has been cleaned. A reticle is selected from the solution of the cleaned reticles may be transported into the contamination analysis unit 20 by means of an automatic carrying machine (not shown) or directly by an operator. The contamination analysis unit 20 may include a sampling module 22 for abstracting the sampling liquid from the reticle, and an analyzer 24 for detecting a degree of contamination.

FIG. 3 is a sectional diagram schematically illustrating an embodiment of the sampling module 22 shown in FIG. 1. The sampling module 22 may comprise a chamber 100, a liquid tub 200, a heating member 400, a temperature detecting member 460, a liquid supplying nozzle 520, and a purge gas supplying member 600. The chamber 100 may provide a space 102 airtight to the external environment. The chamber 100 has a housing 120 and a door 140. The housing 120 may be configured as a parallelepiped tub. On the top of the housing 120, an opening may be provided to permit entrance and exit of the reticle 70. The door 140 may be provided to open and close the opening. The door 140 may be constructed to be operable by rotation.

The chamber 100 may include the liquid tub 200. The liquid tub 200 may have a containing space 220. For example, the liquid tub 200 may be shaped in a parallelepiped plate with the top on which a groove may be formed. The groove is provided in the containing space. Thus, the containing space 220 is formed by a sidewall 222 and a bottom face 224. The reticle 70 moves downward vertically through the opening in the housing 120 and the target side 72 is introduced into the liquid tub 200. The liquid tub 200 may be formed in a size sufficient to accept the target side 72 of the reticle 70. The liquid tub 200 may be made of quartz or other material that will not contaminate the liquid that is filled in the containing space 220. The liquid tub may be supported by a prop 260, being isolated from the bottom of the housing 120.

Stay projections 240 extending upward may be placed in order to prevent the target side 72 of the reticle 70, from contacting with the bottom of the containing space 220. Stay projections 240 may be provided and positioned so as to contact the edge of the reticle 70. The stay projections 240 permit the reticle 70 to be mounted thereon to minimize a contacting area of other faces with the sampling solution and to allow only the target side 72 of the reticle 70 to contact the solution. If the other faces contact the solution, inspection reliability to contamination may be degraded because all of the faces are contacting the solution. Each stay projection 240 may be shaped in a form point-contacting the reticle 70. For example, the stay projection 240 may be shaped in a hemisphere. Locations and shapes of the stay projection are variable in accordance with structural conditions and the selection of location or shape of which will be within the skill of one in the art.

In abstracting a sampling liquid by supplying a solution to the target side 72 of the reticle 70, the inspection reliability could be degraded because the liquid does not contact uniformly with the target side 72. But, according to the present invention, by abstracting the sampling liquid in the condition of steeping or soaking the target side 72 of the reticle 70 in the solution, the inspection reliability may be improved because the target side 72 of the reticle 70 is in uniform contact with the solution.

The liquid tub 200 may be configured to reduce the amount of solution used so that the amount used may be less than 450 milliliters, and often is less than 100 milliliters.

A liquid supply nozzle 520 supplies the solution into the containing space 220 of the liquid tub 200. As an example, the liquid supply nozzle 520 may be disposed to make an inject hole 522 face toward the edge of the containing space 220. The liquid supply nozzle 520 may be comprised of a supply rod 524 inclined upward to the top of the liquid tub 200 from the inner wall of the housing 120, and an inject rod 522 extending downward from the end of the supply rod 520. The inject rod 522 may be positioned so as to not interfere with the reticle 70 while the reticle 70 moves into the containing space 220.

Figure 4:
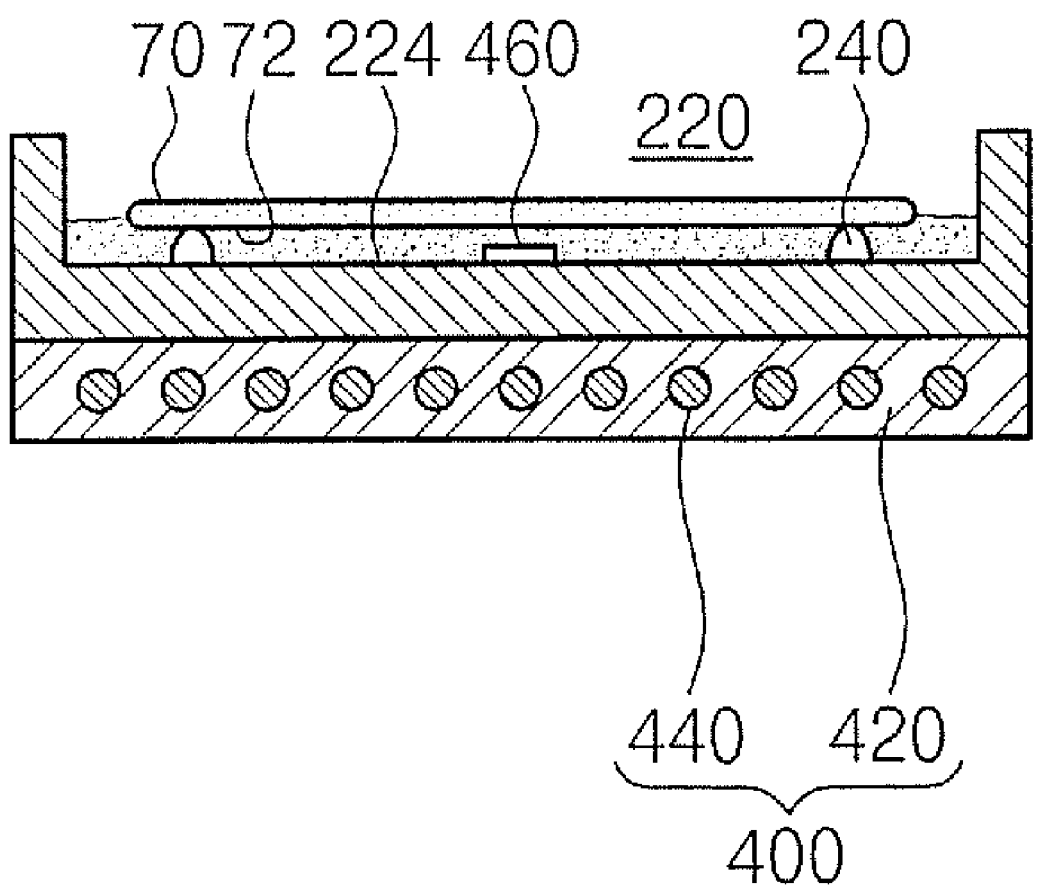
FIG. 4 is a sectional diagram illustrating the configuration of the reticle steeped in the deionized water.

A liquid supply pipe 540 may be located out of the housing 120, connecting a liquid reservoir to the liquid supply nozzle 520 so as to flow the solution from the liquid reservoir into the liquid supply nozzle 520. The liquid supply nozzle 520 may include a valve 542 opening and closing its internal path. Opening and closing the valve 542 may be carried out by the controller 30. The controller 30 opens the valve 542 for a predetermined time so as to regulate an amount of the solution to the containing space 220 at a constant rate. An amount of the solution supplied into the containing space 220 may be set to a rate sufficient to have the target side 72 of the reticle 70 in the solution, but not to allow a counter face of the target side 72 of the reticle 70 to contact the solution. In an embodiment, the amount of solution may be optimized to be as small as possible so as to not contact the side or part of the reticle 70 not steeped in the solution. FIG. 4 illustrates an embodiment wherein the reticle 70 is steeped in the solution.

Different from the aforementioned, the supply of the solution to the containing space 220 may be manually carried out by an operator. But, this manual supply may cause variation in an amount of the solution, degrading the inspection reliability. Therefore, in one embodiment, an opening time of the valve 542 by the controller 30 may be controlled so as to provide an uniform amount of the solution supplied into the containing space 220.

The heating member 400 may heat the solution that is in contact with the target side 72 of the reticle 70. As an example, the heating member 400 may be configured to continuously heat the solution while the target side 72 of the reticle 70 is in contact with the solution. The heating member may be comprised of a heating plate 420 placed under the liquid tub 200 and a heating line 440 inserted in the plate 420. Otherwise, the heating line 400 may be inserted in the liquid tub 200.

On the bottom of the containing space 220 may be set a temperature detecting member 460. The temperature detecting member 460 continuously senses temperature of the solution and a sensed value of temperature is transferred to the controller 30. The controller 30 may be able to control a rate of power supplied to the heating member 440 with reference to the sensed value of temperature.

In abstracting a sampling liquid by contacting the solution room temperature with the target side 72 of the reticle 70, it may be desirable to have a sufficient length of time of contacting the reticle 70 with the solution so as to make pollutants of the target side 72 fully contained in the sampling solution (e.g., deionized water). But, as aforementioned, even with a relatively short time in contacting the target side 72 of the reticle 70 to the heated solution, the pollutants of the target side 72 may be sufficiently contained in the solution. According to an experiment, in the inspection reliability, a case that the target side 72 of the reticle 70 contacts with the solution at about 90° C. for 30 minutes is much better than a case that the target side 72 of the reticle 70 contacts with the solution at about room temperature for 1 hour.

While this embodiment is described about the structure with the heating member 400 installed in the liquid tub 200, the location and kind of the heating member 400 may be modified or altered in various forms as will be within the skill of one in the art.

The heating member 400 may have a heater installed on the liquid supply pipe 540. In this case, it may be necessary to lengthen a time of contacting the target side 72 of the reticle 70 to the solution, in order to obtain the desired inspection reliability, because the temperature of the solution is lowered over time. Thus, in one embodiment, the solution may be continuously heated while the target side 72 of the reticle 70 is in contact with the solution.

The purge gas supplying member 600 may supply a purge gas into the chamber 100. The purge gas supplying member 600 may be comprised of a gas jet nozzle 620 and a gas supply pipe 640. The purge gas may be nitrogen or an inert gas such as helium, neon, argon, krypton, and xenon. The gas jet nozzle 620 may be located at the upper side of the chamber 100. The gas supply pipe 640 may be placed out of the chamber 100, supplying the purge gas through the gas jet nozzle 620. The gas supply pipe 640 may include a valve 642, operated by the controller 30. The purge gas may be jetted into the chamber 100 while the reticle 70 comes in and exits out of the chamber 100 through the door 140. The purge gas in one embodiment may be continuously supplied into the chamber even while the reticle 70 is in contact with the solution. The purge gas acts to minimize an inflow amount of external air into the chamber 100 and exhausts remaining air out of the chamber 100. An exhaust pipe 160 may be connected to the bottom or to the side of the housing 120.

By steeping the reticle 70 in the solution for a predetermined time, a sampling liquid that contains the pollutants from the target side 72 of the reticle 70 may be obtained. The reticle 70 may be removed from the containing space 220 and the sampling liquid is delivered to the analyzer 24. The liquid tub 200 may be configured in a structure separable from the chamber 100. For example, the liquid tub 200 may be mounted in the heating member 400 or the prop 260, fixed to the heating member 400 or the prop 260 by means of a jointing member (not shown). In this case, with the sampling liquid, the operator separates the liquid tub 200 from the chamber 100 and provides the sampling liquid to the analyzer 24.

Figure 5:
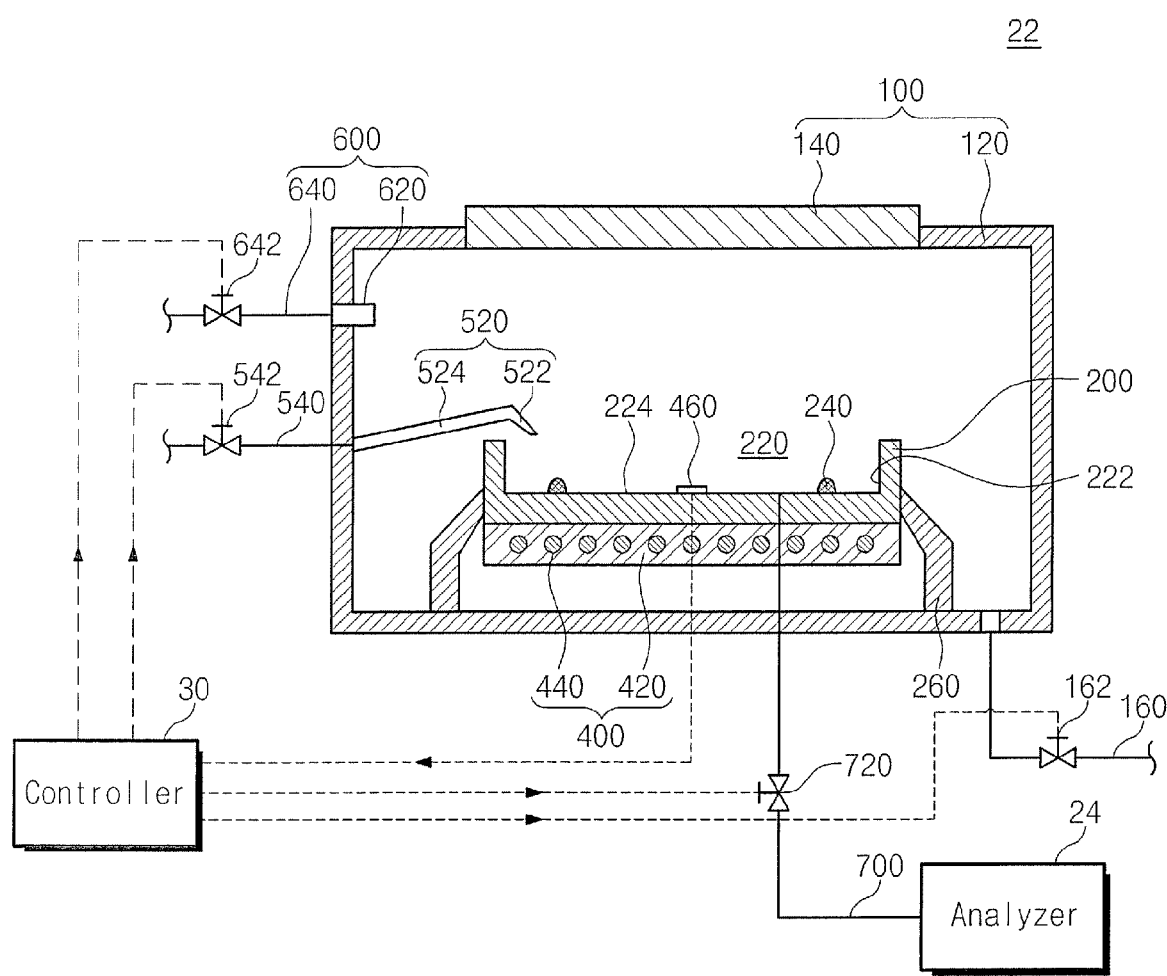
FIG. 5 is a sectional diagram schematically illustrating another embodiment of the sampling module shown in FIG. 1.

Selectively, as shown in FIG. 5, the liquid tub 200 may also be connected to a liquid outflow pipe 700. The liquid outflow pipe 700 may be provided to supply the sampling liquid into the analyzer 24. The liquid outflow pipe 700 may include a valve 720 opening and closing its internal path. The valve 720 may be operated by the controller 30.

The analyzer 24 detects pollutants such as ammonium ($NH_3$), sulfuric oxide ($SO_x$), and various organic substances. The analyzer 24 may be an HPIC analyzer, such as those known to one skilled in the art.

A result of inspection by the analyzer 24 may be transferred to the controller 30. If the inspection result informs that concentration of contamination is within a permissible range, the controller 30 may provide the reticle 70 to the semiconductor fabrication exposing apparatus (not shown) and the fabrication exposing process may be kept going. Otherwise, if the concentration of contamination is out of the permissible range, an alarm 40 may inform the operator of that contamination. Additionally, the controller 30 may operate to control migration of the reticle 70 so as to re-clean the reticle 70 if necessary. The controller 30 may be able to correct a cleaning recipe, e.g., an amount or concentration of cleaning liquid or a cleaning time.

In the above description, it is described such that the operator controls the entrance and exit of the reticle 70 in and out of the sampling module 22. But, it is also possible to provide an automatic mechanism (not shown) including a robot automatically controlling movement of the reticle 70, such as the entrance/exit into/from the sampling module 22, and transportation by the cleaning apparatus 10 and the sampling module 22.

Figure 6:
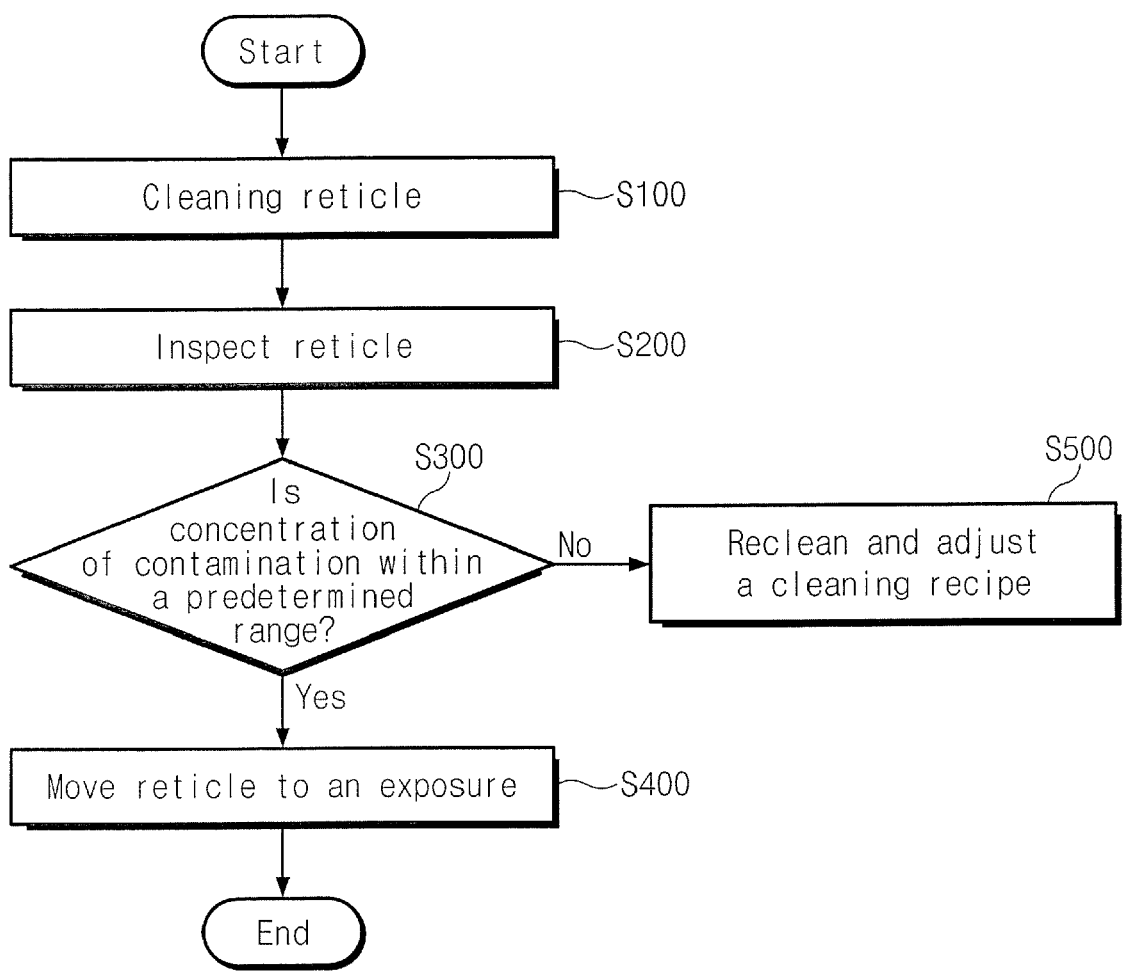
FIG. 6 is a flow chart showing a procedure of cleaning the reticle.
Figure 7:
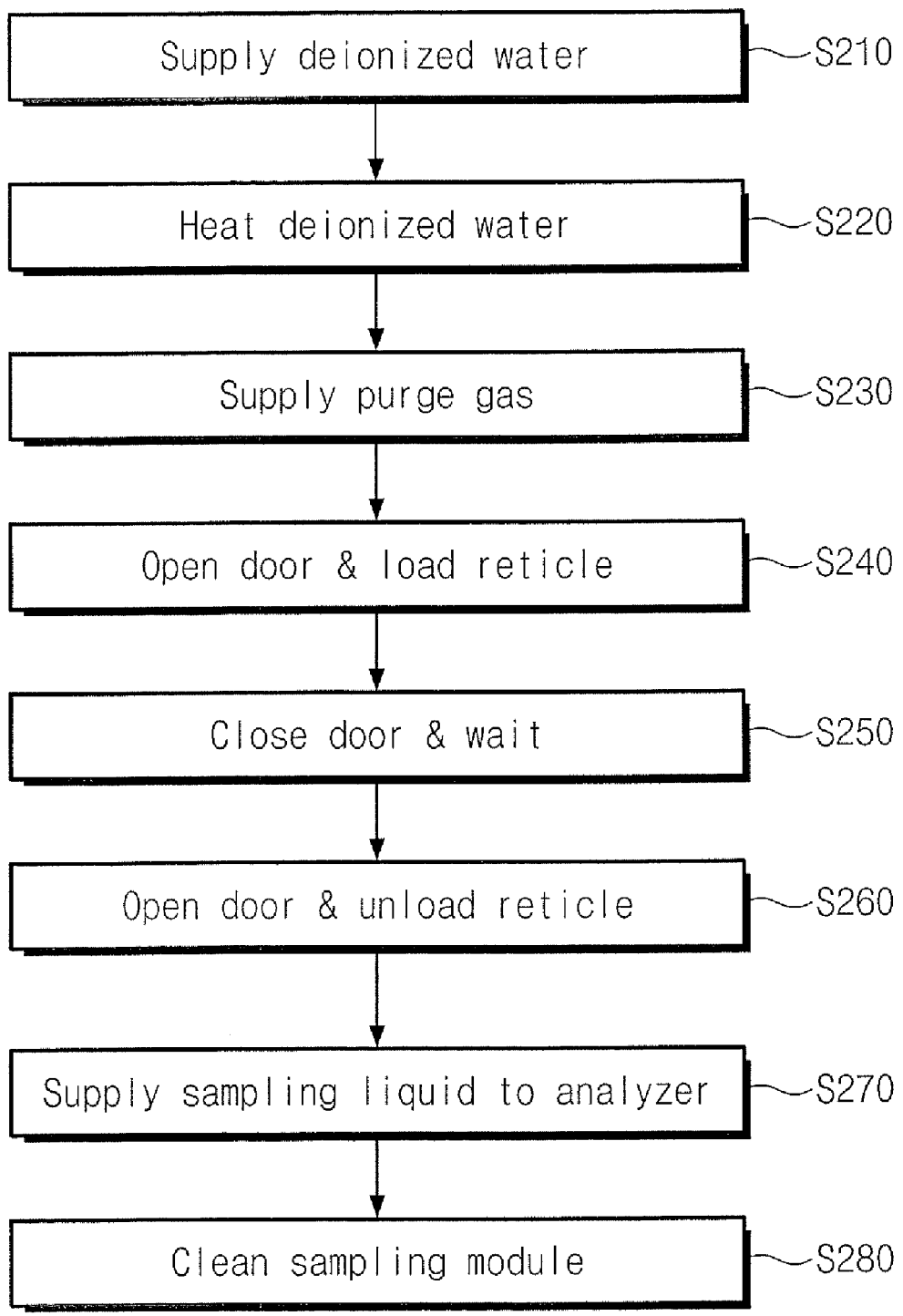
FIG. 7 is a flow chart of the reticle inspecting procedure shown in FIG. 6.

Hereinafter will be described a method of cleaning the reticle 70 in conjunction with FIGS. 6 through 15. FIG. 6 is a flow chart showing a procedure of cleaning the reticle and FIG. 7 is a flow chart of the reticle inspecting procedure shown in FIG. 6. FIGS. 8 through 15 are sectional diagrams sequentially illustrating the reticle inspecting procedure. Among the valves 162, 542, and 642, the unshaded valves denote that their corresponding paths are open, while the shaded valves denote that their corresponding paths are closed.

The reticles treated by the exposing apparatus may be transported into the cleaning apparatus. The reticle may be cleaned while passing through the units of the cleaning apparatus (step S100). After cleaning the reticle by chemical means, a step of rinsing the reticle by deionized water may be repeated a plurality of times and in the last step the reticle may be dried.

Figure 8:
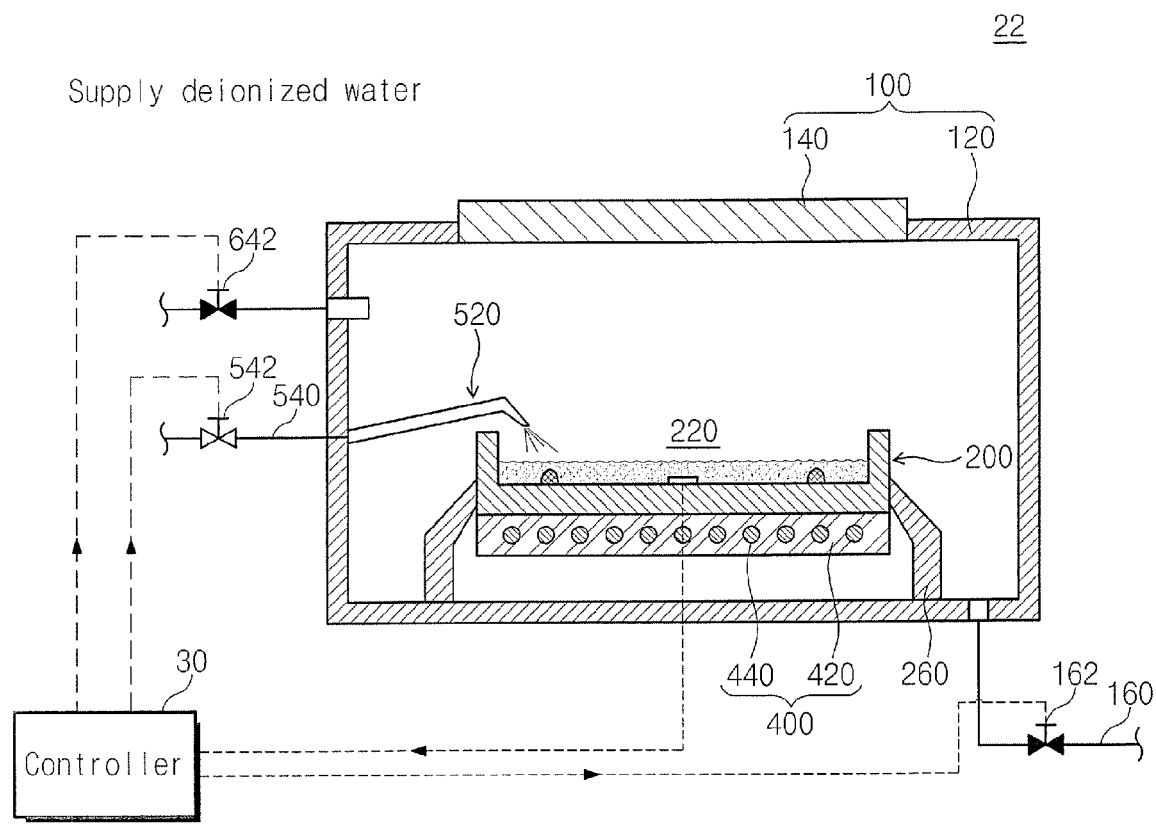
FIGS. 8 through 15 are sectional diagrams sequentially illustrating various embodiments of the reticle inspecting procedure.

Once pluralities of the reticles are cleaned, one of the reticles may be put into the inspection to find whether it has been successfully cleaned to a required level (step S200). As shown in FIG. 8, first, the solution (deionized water) may fill the containing space 220 of the liquid tub 200 placed in the sampling module 22 (step S210). The solution may be supplied to the containing space 220 by way of the liquid supply nozzle 520. The controller 30 may adjust an opening time of the valve 542 so as to supply the solution to the containing space 220 in a predetermined amount.

Figure 9:
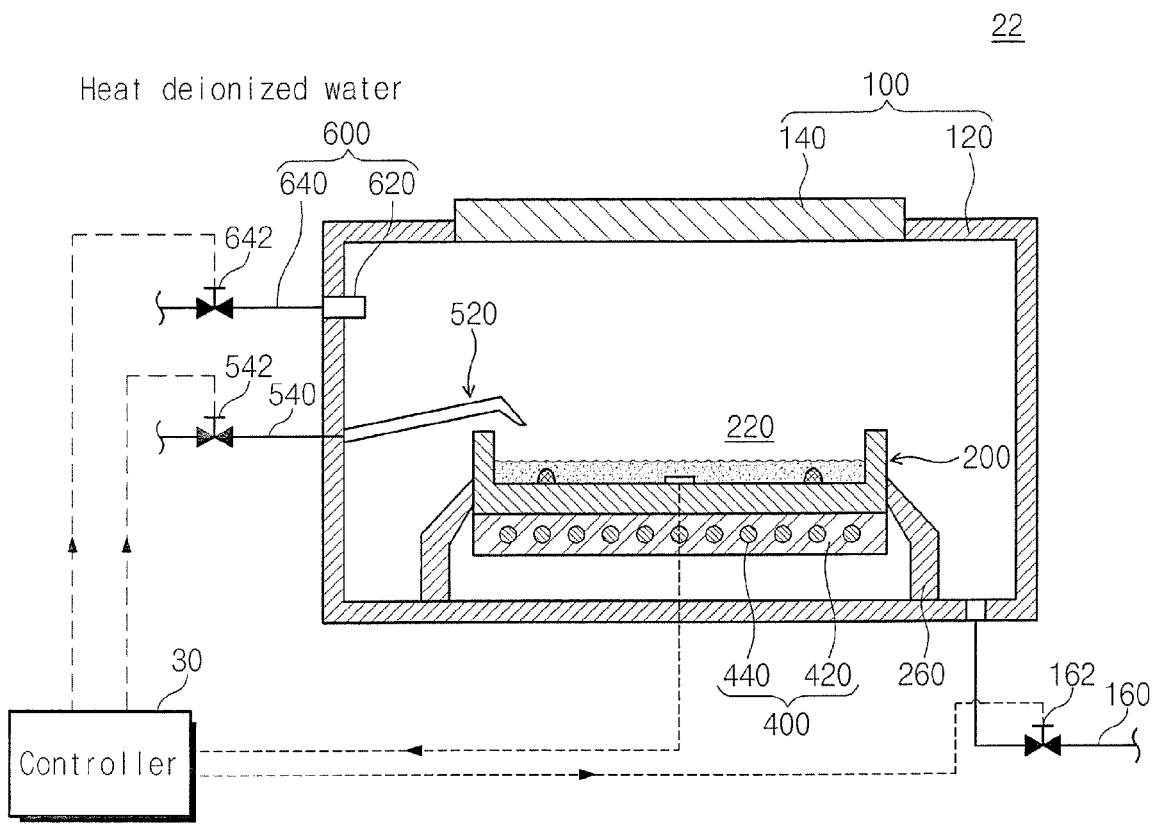

Then, referring to FIG. 9, the solution filling the containing space 220 may be heated to a predetermined temperature (step S220). As an example, the predetermined temperature may be about 90° C.

Figure 10:
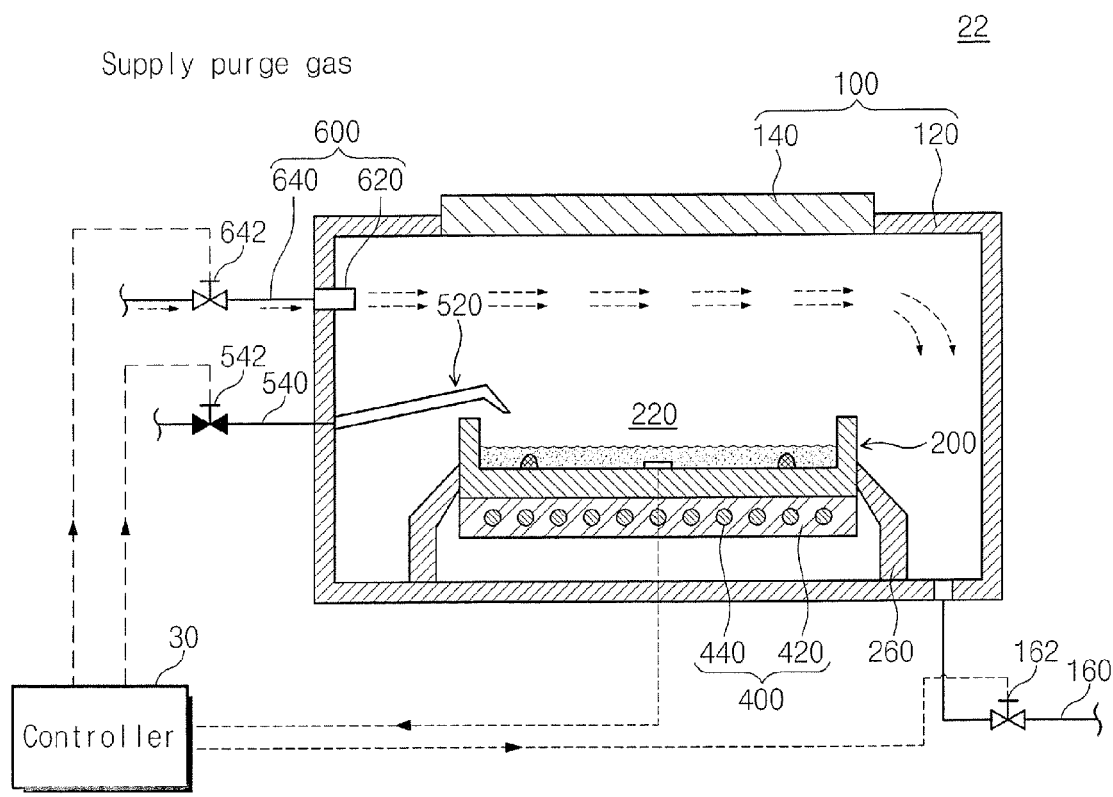

Next, referring to FIG. 10, a purge gas may be supplied into the chamber 100 through the gas supply nozzle 620 (step S230). The supply of the purge gas may precede the supply or heating of the solution.

Figure 11:
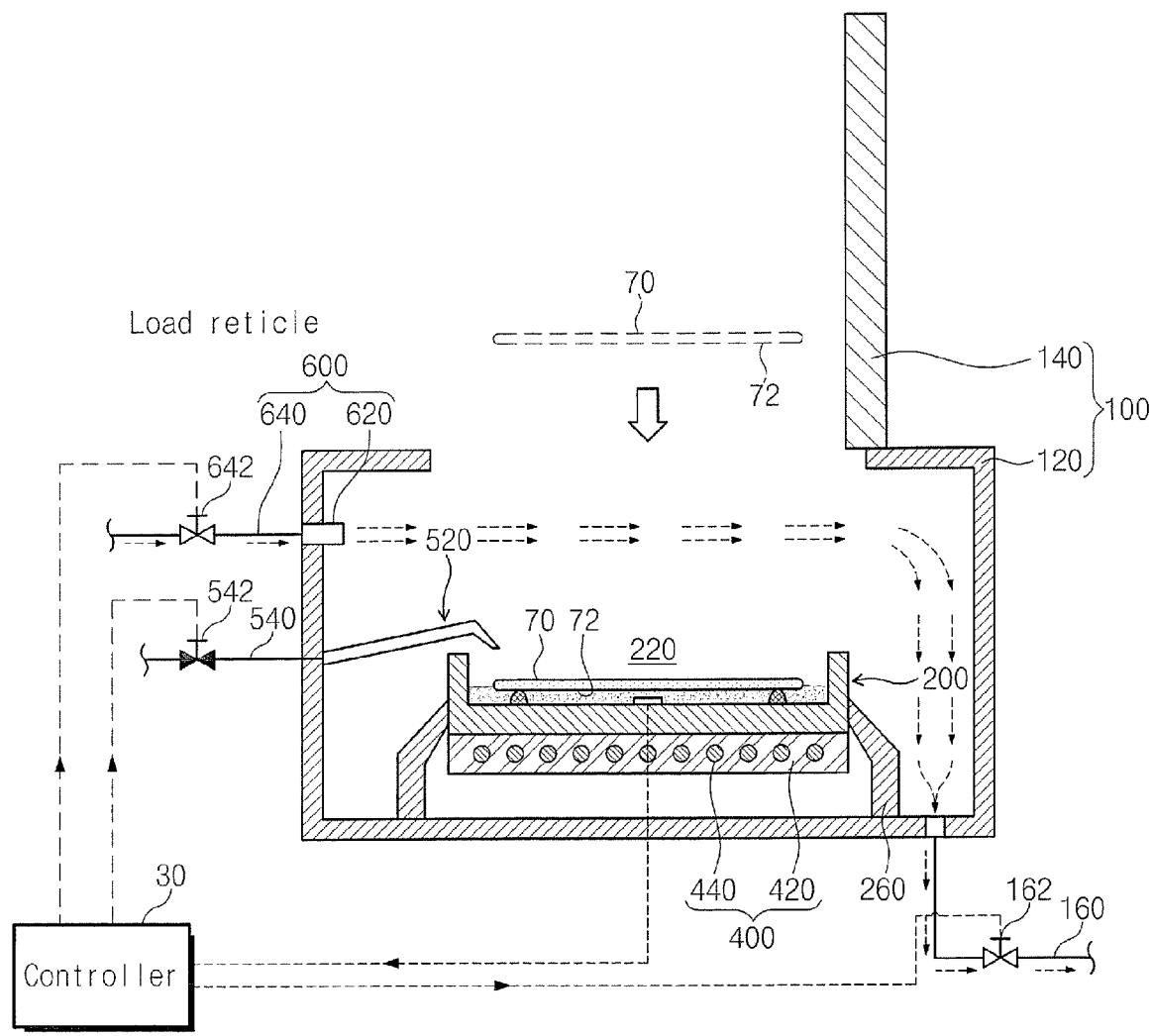

Thereafter, referring to FIG. 11, the upper side of the housing 120 may be opened by the door 140 of the chamber 100 and the reticle 90 may be introduced into the chamber 100 (step S240). The reticle 70 moves down vertically with the target side 72 facing downward, being laid on the stay projections 240 of the containing space 220. The movement of the reticle 70 may be conducted by the operator or a carrying robot.

Figure 12:
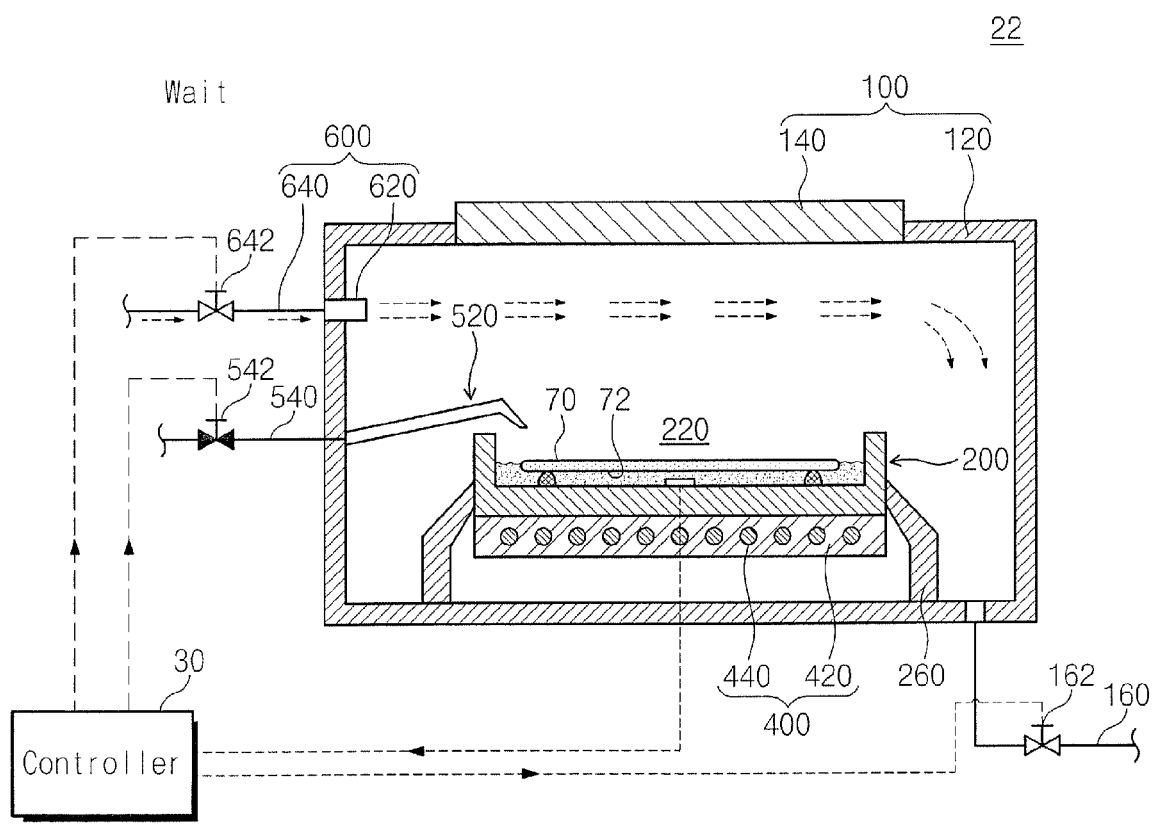

Then, as illustrated in FIG. 12, the target side 72 of the reticle 70 may be steeped in the solution for a predetermined time (step S250). For example, the predetermined time may be about 30 minutes. While the reticle 70 is being steeped in the solution, the solution may be continuously heated to maintain the predetermined temperature.

Figure 13:
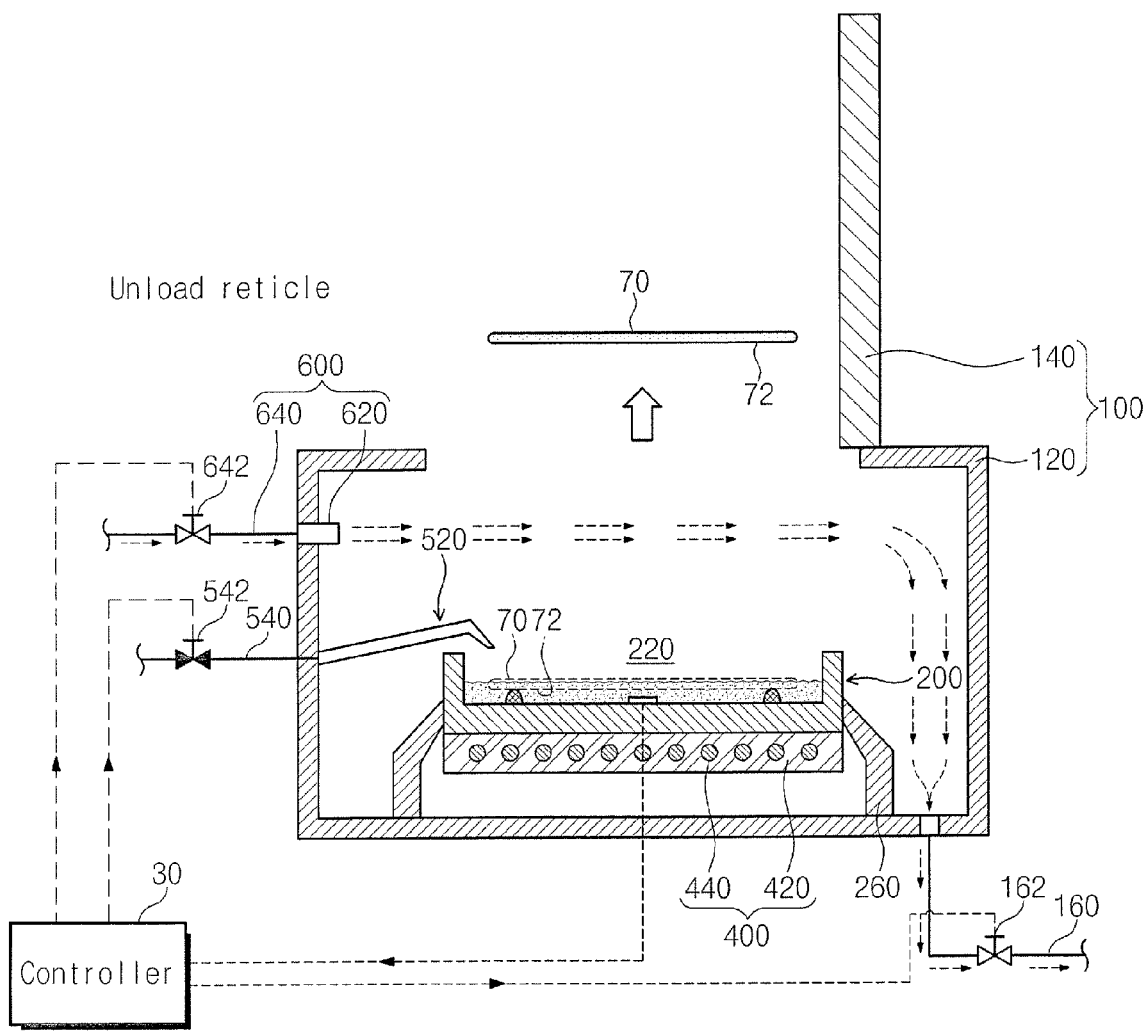

After the predetermined time, referring to FIG. 13, the top of the housing is opened by the door 140 of the chamber 100 and the reticle 70 is drawn out of the chamber 100 (step S260). The purge gas supply as shown in FIG. 10 may still be carried out without interruption.

Figure 14:
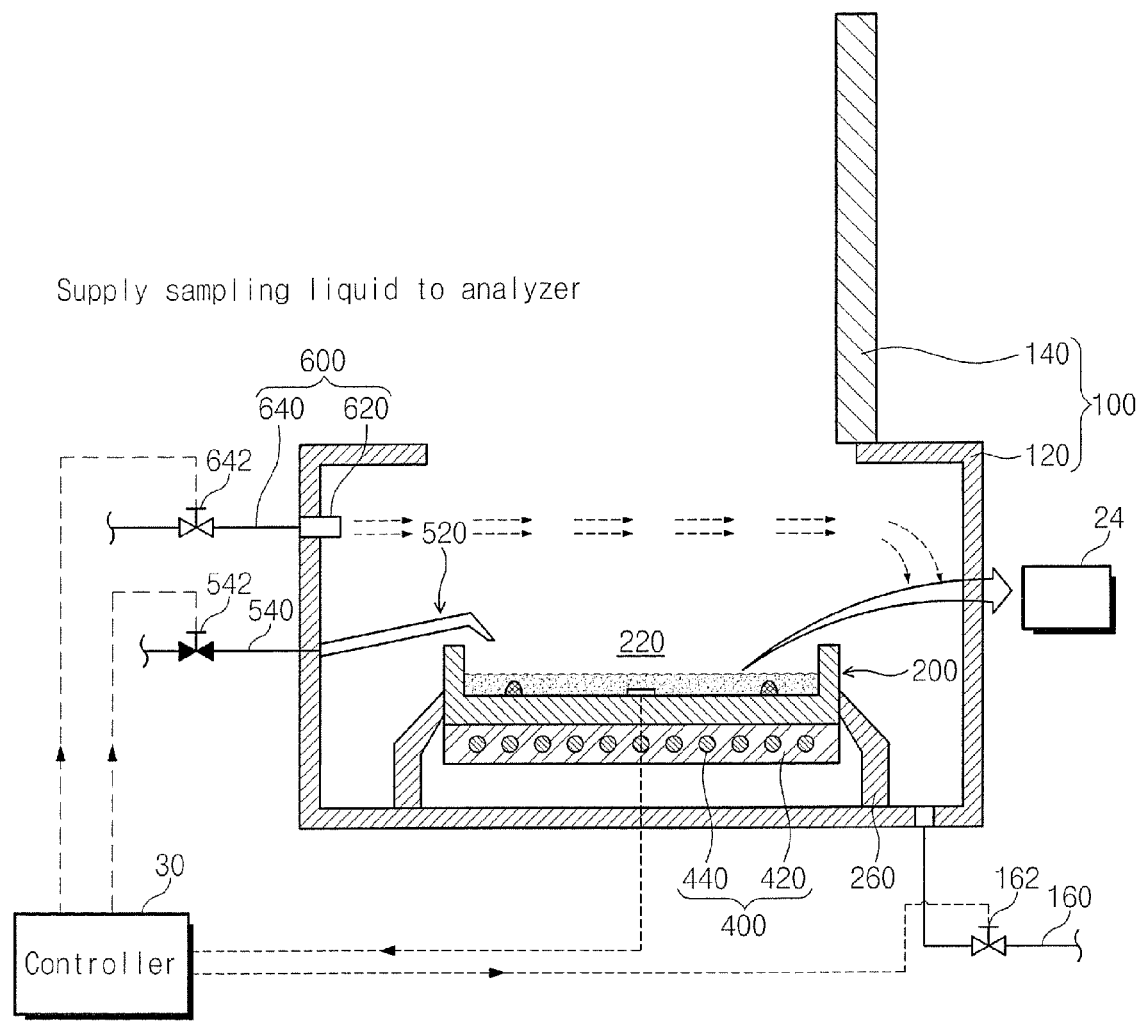

Next, as illustrated in FIG. 14, the sampling liquid remaining in the containing space 220 may be provided to the analyzer 24 (step S270). By using the sampling module shown in FIG. 3, the operator may be able to manually supply the sampling liquid to the analyzer 24 after separating the liquid tub 200 from the chamber 100. By using the sampling module shown in FIG. 5, the sampling liquid may be supplied into the analyzer 24 by way of the outflow pipe 700 connected to the liquid tub 200.

Figure 15:
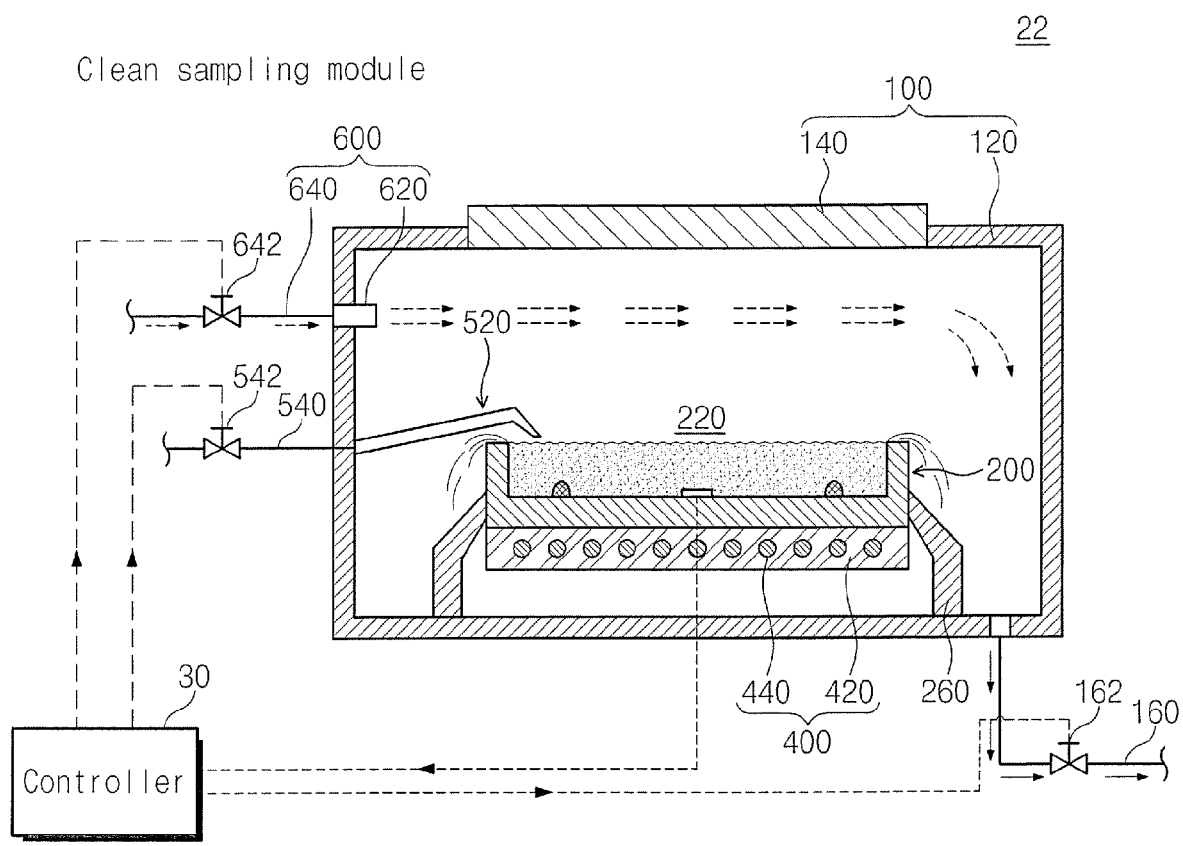

Referring to FIG. 15, after closing the door 140 of the chamber 100, the purge gas may be supplied into the chamber 100 and a cleaning solution may be supplied to clean the inside of the sampling module (step S280). The purge gas and the cleaning solution are discharged out of the chamber 100 through the exhaust pipe 160. The cleaning solution may be supplied through the liquid supply nozzle 520, or another nozzle different from the liquid supply nozzle 520, into the containing space 220 of the liquid tub 200.

The analyzer 24 may inspect concentration of contamination from the sampling liquid and results of the inspection may be transferred to the controller 30 (step S300). The controller 30 may transport the reticle 70 to the exposing apparatus if the concentration of contamination is within a permissible range (step S400). If concentration of contamination is out of the permissible range, the controller 30 may generate an alarm and the reticle may be transported back into the cleaning apparatus 10 and then re-cleaned. During this, the controller 30 may be able to correct the recipe of the cleaning apparatus 10 (step S500).

According to some embodiments of the present invention, the inspection reliability in analyzing pollutants remaining on the target side of an object to be inspected, such a reticle, after cleaning the reticle may be improved.

Further, according to embodiments of the present invention, inspection reliability may be improved by minimizing an area of contact of the other faces, except for the target side of the reticle.

Further, according to embodiments of the present invention, inspection reliability may be improved by abstracting the sampling liquid while steeping the target side of the reticle in the solution.

Further, according to embodiments of the present invention, the time for analyzing pollutants that remain on the target side of the reticle after cleaning the reticle may be reduced.

Moreover, since the reticle is re-cleaned or the cleaning recipe is corrected unless the reticle has not been cleaned to the desired level, embodiments of the present invention assure high reliability in cleaning the reticle.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A contamination analysis unit for inspecting pollutants on a target side of an inspection object, comprising:
    a sampling module for abstracting a sampling liquid provided by contacting the target side of the inspection object with a solution; and
    an analyzer configured red to analyze pollutants in the sampling liquid,
    wherein the sampling module comprises:
    a chamber providing a space that is isolated from the external environment;
    a liquid tub provided in the chamber and having a containing space that accommodates the target side of the inspection object; and
    a liquid supply nozzle configured to supply the solution into the containing space of the liquid tub,
        wherein the chamber comprises a housing with a side having a path through which the inspection object is introduced and a door opening and closing the path.

2. The contamination analysis unit as set forth in claim 1, wherein the sampling module further comprises a purge gas supplying member configured to supply a purge gas into the chamber.

3. The contamination analysis unit as set forth in claim 1, wherein the sampling module further comprises a heating member configured to heat the solution in the containing space.

4. The contamination analysis unit as set forth in claim 1, wherein the sampling module further comprises a temperature detecting member sensing temperature of the solution in the containing space.

5. The contamination analysis unit as set forth in claim 3, wherein the containing space is prepared by forming a groove at the upper side of the liquid tub,
    wherein the door is placed on the top of the housing, opposite to the containing space.

6. The contamination analysis unit as set forth in claim 5, wherein the liquid tub comprises stay projections supporting the inspection object in the containing space so as to isolate the target side of the inspection object from the bottom of the containing space.

7. The contamination analysis unit as set forth in claim 1, wherein the sampling module further comprises: an exhaust pipe connecting the containing space to the analyzer so as to provide the abstracted liquid sampling from the sampling module to the analyzer.

8. The contamination analysis unit as set forth in claim 1, wherein the sampling module is shaped to abstract the sampling liquid from a reticle that is used in a semiconductor process as the inspection object.

9. A method for analyzing contamination in a target side of an inspection object comprising:
    loading the inspection object into a chamber through a path which is provided at a side of the chamber and is open and closed by a door;
    obtaining a sampling liquid by;
    filling the solution in a containing space formed on a top of a liquid tub provided in the chamber, and steeping the target side of the inspection object in the solution while heating and after facing the target side of the inspection object toward the solution filling the liquid tub, so that the side opposite of the target side is apart from the solution;
    analyzing contamination through inspecting the sampling liquid; and
    wherein the sampling liquid is obtained from an airtight space and a purge gas spreads in the space while the inspection object is being positioned in the space.

10. The contamination analysis method as set forth in claim 9, wherein an opening time of a valve installed in a liquid supply pipe for supplying the solution into the containing space is regulated by a controller so as to provide an uniform amount of the solution filling the containing space.

11. The contamination analysis method as set forth in claim 9, wherein the inspection object is a reticle.

12. A reticle cleaning system comprising:
    a cleaning apparatus configured to clean a reticle; and
    a contamination analysis unit configured to inspect pollutants remaining on a target side of the reticle that has been washed by the cleaning apparatus,
    wherein the contamination analysis unit comprises:
    a chamber;
    a liquid tub provided into the chamber, including a containing space accommodating the target side of the reticle;
    a liquid supply nozzle configured to supply a solution into the containing space of the liquid tub; and
    an analyzer configured to analyze pollutants from a sampling liquid obtained by steeping the target side of the reticle in the solution,
    wherein the chamber comprises a housing with a side having a path through which the reticle is introduced and a door opening and closing the path.

13. The reticle cleaning system as set forth in claim 12, wherein the contamination analysis unit further comprises a purge gas supplying member configured to supply a purge gas into the chamber.

14. The reticle cleaning system as set forth in claim 12, wherein the contamination analysis unit further comprises a heating member configured to heat the solution in the containing space.

15. The reticle cleaning system as set forth in claim 12, which further comprises a controller receiving an analyzed result from the analyzer and adjusting a recipe of the cleaning apparatus with reference to the analyzed result.

* * * * *